(12) United States Patent
Fitzgerald et al.

(10) Patent No.: US 8,673,652 B2
(45) Date of Patent: Mar. 18, 2014

(54) IMMUNOASSAY WITH EXTENDED DETECTION WINDOW

(75) Inventors: Stephen Peter Fitzgerald, Crumlin (GB); Robert Ivan McConnell, Crumlin (GB); Philip Andrew Lowry, Crumlin (GB); Elouard Benchikh, Crumlin (GB)

(73) Assignee: Randox Laboratories Limited (IE)

( * ) Notice: Subject to any disclaimer, the term of this patent is extended or adjusted under 35 U.S.C. 154(b) by 281 days.

(21) Appl. No.: 13/019,276

(22) Filed: Feb. 1, 2011

(65) Prior Publication Data

US 2011/0189794 A1 Aug. 4, 2011

(30) Foreign Application Priority Data

Feb. 2, 2010 (EP) .................................... 10152365

(51) Int. Cl.
*G01N 33/566* (2006.01)
*C07K 14/765* (2006.01)
*C07K 16/18* (2006.01)
*C12N 9/96* (2006.01)

(52) U.S. Cl.
USPC ......... 436/501; 435/188; 530/405; 530/389.8

(58) Field of Classification Search
None
See application file for complete search history.

(56) References Cited

U.S. PATENT DOCUMENTS

2003/0170728 A1* 9/2003 McConnell et al. ........... 435/7.1

OTHER PUBLICATIONS

Hollis et al., "Determination of vitamin D status by radioimmunoassay with an 125I-labeled tracer," Clin. Chem., 1993, vol. 39, pp. 529-533.*
Klupsch et al., "Major Metabolites of Zolpidem: Expeditious Synthesis and Mass Spectra," Chem. Pharm. Bull., 2006, vol. 54, No. 9, pp. 1318-1321.*
D. A. Khan, et al., "Lead Related Occupational Workers are Potential Source of Elevated Blood Lead in their Children," Clinical Chemistry, vol. 55, No. 6, Supplement (2009), p. A250.
I. De Clerck et al., "Development of a RadioImmunoassay for the Determination of Zolpidem in Biological Samples," Analyst, vol. 122, (Oct. 1997) pp. 1119-1124.
K. Huynh et al., "Development of a Homogeneous Immunoassay for the Detection of Zolpidem in Urine," Journal of Analytical Toxicology, vol. 33, (Oct. 2009) pp. 486-490.
L. Reidy, et al., "The Incidence of Zolpidem Use in Suspected DUI Drivers in Miami-Dade Florida: A Comparative Study Using Immunalysis zolpidem ELISA Kit and Gas Chromatography-Mass Spectrometry Screening, Journal of Analytical Toxicology", vol. 32, (Oct. 2008) pp. 688-694.
V. Ascalone et al., "Determination of xolpidem, a new sleep-inducing agent, and its metabolites in biological fluids: pharmacokinetics, drug metabolism and overdosing investigations in humans," Journal of Chromatography, vol. 581, (1992) pp. 237-250.
B. Ahrens et al., "Screening, Identification and Determination of the Two New Hynotics Zolpidem and Zopiclone," Arzneim-Forsch/Drug Res. 44 (II), Nr. 7, (1994) pp. 799-802.
J. Lewis, et al, "A Simple and Rapid Method for the Identification of Zolpidem Carboxylic Acid in Urine," Journal of Analytical Toxicology, vol. 31, (May 2007) pp. 195-199.
G. Hempel et al., "Direct determination of zolpidem and its main metabolites in urine using capillary electrophoresis with laser-induced fluorescence detection," Journal of Chromatography B, vol. 675, (1996) pp. 131-137.
M. Villain et al., "Windows of detection of zolpidem in urine and hair: application to two drug facilitated sexual assaults," Forensic Science International, vol. 143, (2004) pp. 157-161.
L. von Moltke, et al. Zolpidem metabolism in vitro: responsible cytochromes, chemical inhibitors, and in vivo correlations, British Journal of Clinical Pharmacology, 48, (1999) pp. 89-97.
B. Madea et al., Knock-Out Drugs: their Prevalence, Modes of Action, and Means of Detection, Medicine, Review Article, Deutsches Arzteblatt International, 106(20), (2009) pp. 341-347.
C. Maravelias, PhD. et al., "Drug-Facilitated Sexual Assault Provoked by the Victim's Religious Beliefs," A Case Report, American Journal of Forensic Medicine Pathol., vol. 30, No. 4, (Dec. 2009) pp. 384-385.
C. Victorri-Vigneau, et al., "Evidence of zolpidem abuse and dependence: results of the French Centre for evaluation and Information on Pharmacodependence (CEIP) network survey, British Journal of Clinical Pharmacology", British Journal of Clinical Pharmacology, 64:2, (2007) pp. 198-209.
P. Salvà et al., "Clinical Pharmacokinetics and Pharmacodynamis of Zolpidem ," Drug Disposition, Clinical Pharmacokinet, 29(3), (1995) pp. 142-153.
K. Huynh et al., Oklahoma, Program and Abstracts, SOFT 2009, Oct. 19-23 (2009).
European Search Report issued by the European Patent Office on Sep. 14, 2010 in European Appl. No. EP10152365.2.

* cited by examiner

*Primary Examiner* — Shafiqul Haq
*Assistant Examiner* — Galina Yakovleva
(74) *Attorney, Agent, or Firm* — Stoel Rives LLP; Samuel E. Webb

(57) ABSTRACT

The immunoassay method and kit are provided for the detection and/or the determination of zolpidem. The disclosure provides novel antibodies, derived from a novel immunogen, that are highly sensitive and bind to zolpidem and its main urinary metabolite [3-(2-N,N-dimethylamino-2-oxoethyl)-6-methylimidazo[1,2-a]pyridin-2-yl]benzoic acid, enabling an extension of the detection window of zolpidem in individuals who have abused the drug, or have been victim of its side-effects or its criminal misuse.

3 Claims, 3 Drawing Sheets

IMMUNOASSAY WITH EXTENDED DETECTION WINDOW

CROSS-REFERENCE TO RELATED APPLICATIONS

This application claims the benefit under 35 U.S.C. §119 (a)-(d) of European Patent Application No. 10152365.2, which was filed on Feb. 2, 2010, the entire contents of which are hereby incorporated by reference herein.

TECHNICAL FIELD

The present disclosure relates generally to an immunassay with an extended detection window. The present disclosure also relates to related methods and kits.

BACKGROUND

Zolpidem, systematic name N,N-dimethyl-2-[6-methyl-2-(4-methylphenyl)imidazo[1,2-a]pyridin-3-yl]acetamide, is a widely prescribed drug designed to counteract sleep and brain disorders, notably insomnia. The drug is classed as a non-benzodiazepine hypnotic and acts on the gabba aminobutyric acid receptors. Upon ingestion, zolpidem is fast-acting and has a half-life of 1.5-3 hours. Metabolism is mediated by cytochrome P450, producing more than 80% 4-[3-(2-N,N-dimethylamino-2-oxoethyl)-6-methylimidazo[1,2-a]pyridin-2-yl]benzoic acid (M1) formed via the corresponding hydroxy metabolite, and a relatively smaller amount of 3-(2-N,N-dimethylamino-2-oxoethyl)-2-(4-methylphenyl)imidazo[1,2-a]pyridin-6-yl carboxylic acid (1-4). Despite its proven therapeutic effectiveness there have been increasing reports of dependence, recreational and criminal abuse (5-7) and of life-threatening side-effects due to hallucinations and impaired driving (8). Villain et al (9) report zolpidem to be ranked first in a list of drugs used in drug-facilitated sexual assault. This potential for adverse events or abuse in individuals taking or with access to zolpidem creates a need in clinical and forensic toxicology for its detection and/or determination using practical and inexpensive analytical methods.

Analytical methods that have been used to detect and determine zolpidem include HPLC, LC-MS-MS, GC and GC-MS. A complex and equipment-intensive, column-switching HPLC method incorporating a clean-up and pre-concentration phase targeted M1 as a marker of overdose as it is the most abundant zolpidem marker in both plasma and urine (1). A GC-MS method requiring sample extraction and compound derivatisation is described for detecting M1 for up to 72 hours in two cases of alleged zolpidem drug-facilitated assault (10). The less costly and practical immunoassay has also been used to detect and quantify zolpidem. The immunoassay has many advantages over other mainstream analytical formats such as GC-MS and LC-MS including cost, ease of use and its amenability for manufacture in a compact, portable format for at the scene use. A radioimmunoassay (RIA) and an EMIT-type assay have been described. The RIA describes an immunogen in which the protein crosslinker is incorporated at the 3-position of the fused heterocycle which results in detection of zolpidem, with no reported cross-reactivity towards the metabolites (11). The RIA is extremely sensitive but has associated health and safety issues. Generally, RIAs have low commercial uptake and the inventors are not aware of a commercially available zolpidem RIA. A commercial kit is available for zolpidem forensic screening in whole blood, serum and urine that has a detection cut-off value of 25 ng/ml (Catalog 233 ELISA zolpidem insert, Immunalysis). The kit was reported not to detect M1 at 1000 ng/ml (8). A follow-on immunoassay developed by the same company for the detection of zolpidem in urine reports a detection limit of 5 ng/ml and a detection window of eight hours in an individual described as an infrequent user; at 16 hours zolpidem could not be detected (12). A commercial ELISA kit produced by International Diagnostic Systems detects zolpidem at 75 ng/ml. None of the kits report detection of M1.

Due to zolpidem's rapid and varied inter-individual metabolism (8, 9, 12), the current immunoassays detecting only the parent molecule are insufficiently sensitive to be used reliably as a screening tool for detecting zolpidem mis-use and drug-impaired driving in patient samples beyond approximately 8-24 hours. To overcome this inadequacy, the inventors devised and developed an immunoassay based on detection of zolpidem and its main metabolite M1. The disclosure enables the sensitive immuno-detection and determination of zolpidem and its main metabolite in patient samples, and extends the time period in which zolpidem can be detected following ingestion.

To the extent that the following publications do not conflict with the teachings of the present disclosure, they are incorporated herein by reference:

1. Ascalone V. et al. (1992). *J. Chromatogr.* 581: 237-250
2. Hempel G. and Blaschke G. (1996). *J. Chromatogr. B* 675: 131-137
3. von Moltke L. et al. (1999). *Br. J. Clin. Pharmacol.* 48: 89-97
4. Salva P. and Costa J. (1995). *Clin Pharmacokin.* 29: 142-153
5. Madea B. and Mußhoff F. (2009). *Dtsch. Arztebl. Int.* 106:341-347
6. Maravelias C et al. (2009). *Am. J. Forensic Med. Pathol.* 30: 384-385
7. Victorri-Vigneau C. et al. (2007). *Br. J. Clin. Pharmacol.* 64: 198-209
8. Reidy L. et al (2008). *J. Anal. Tox.* 32: 688-694
9. Villain M. et al. (2004). *Forensic Sci. Int.* 143: 157-161
10. Lewis J. and Vin J. (2007). *J. Anal. Tox.* 31: 195-199
11. De Clerck I. and Daenens P. (1997). *The Analyst* 122: 1119-1124
12. Huynh K. et al. SOFT 2009, Oct. 19-23, 2009, Oklahoma, Program and Abstracts

BRIEF DESCRIPTION OF THE DRAWINGS

The disclosure makes reference to the accompanying drawings, wherein.

SUMMARY

Figure 1:
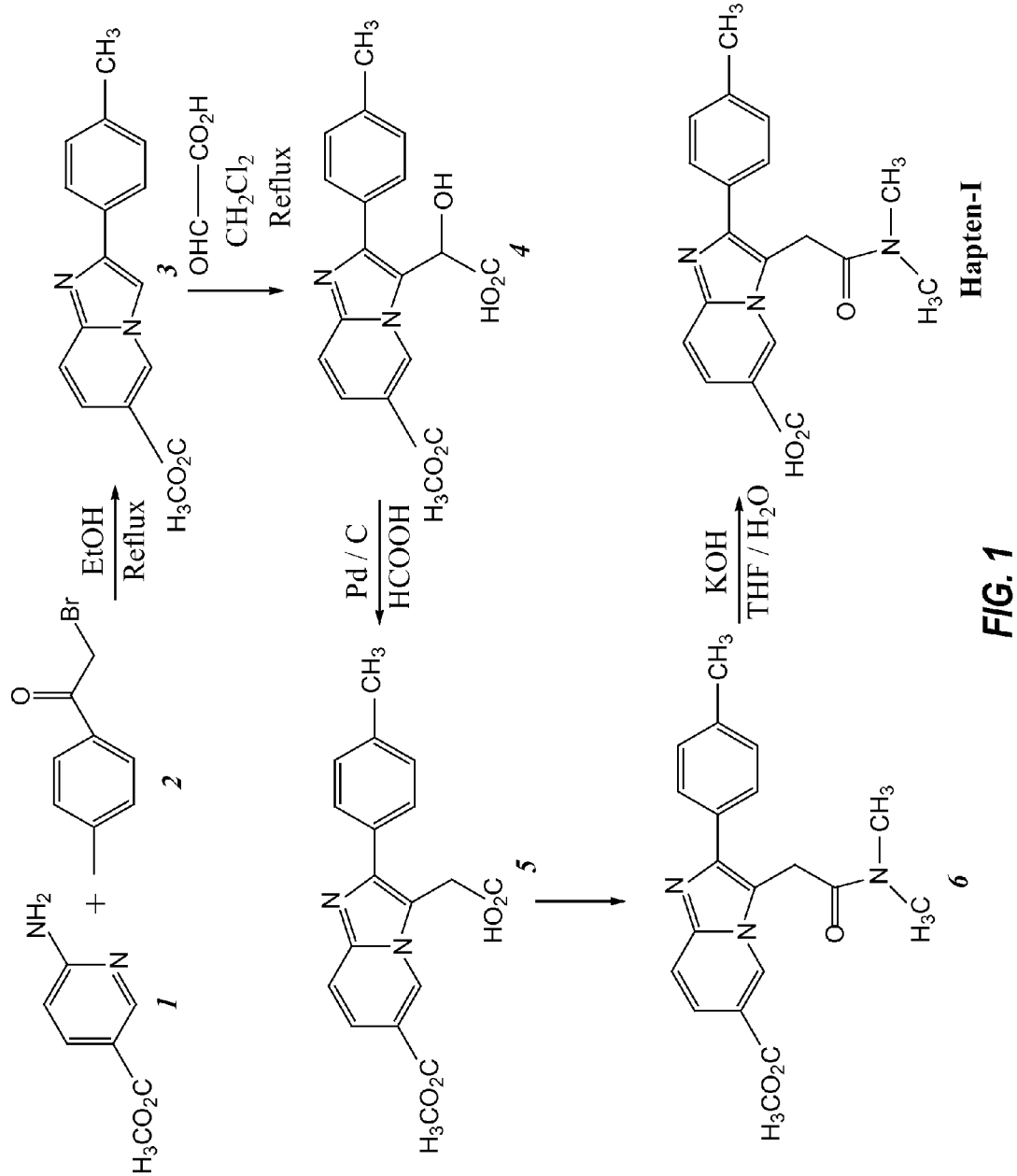
FIG. 1 shows the synthesis of hapten I.

There lacks an immunoassay for the detection and determination of zolpidem in in vitro patient samples that has an extended detection window. The present disclosure provides a solution to this problem. The disclosure makes use of a unique, highly sensitive antibody that binds to zolpidem and its main metabolite, 4-[3-(2-N,N-dimethylamino-2-oxoethyl)-6-methylimidazo[1,2-a]pyridin-2-yl]benzoic acid.

Recognition of 4-[3-(2-N,N-dimethylamino-2-oxoethyl)-6-methylimidazo[1,2-a]pyridin-2-yl]benzoic acid by the highly sensitive antibody of the disclosure enables methods and kits for zolpidem detection and determination that possess an extended detection window compared to other immunoassays. Such methods and kits can be applied, for example, in toxicological screening and drug-facilitated rape cases.

According to a first aspect of the disclosure there is an immunogen of the structure I:

Structure I

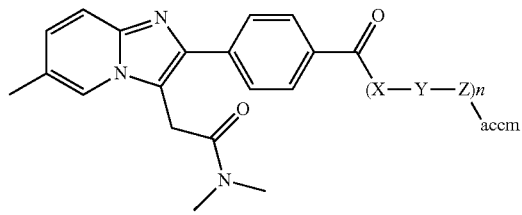

wherein,
accm is an antigenicity conferring carrier material; n=0 or 1; X is a heteroatom, such as nitrogen, oxygen or sulphur; Y is a $C_{1-10}$, which in some embodiments is $C_{2-6}$, substituted or unsubstituted straight-chain alkylene or arylene moiety; Z is, before conjugation with the accm, carboxy, a dithiopyridyl, a maleimide, an amino, a hydroxyl, a thiol, a thioester or an aldehyde moiety.

According to a second aspect of the disclosure, there is an antibody raised against an immunogen of claim 1, which is able to bind to an epitope of zolpidem and 4-[3-(2-N,N-dimethylamino-2-oxoethyl)-6-methylimidazo[1,2-a]pyridin-2-yl]benzoic acid.

According to a third aspect of the disclosure, there is a method of detecting or determining zolpidem and/or 4-[3-(2-N,N-dimethylamino-2-oxoethyl)-6-methylimidazo[1,2-a]pyridin-2-yl]benzoic acid in a solution or an in vitro sample taken from a patient, comprising contacting the solution or sample with an antibody of any of the present disclosure and a conjugate, measuring a detectable signal generated form the conjugate upon binding of the antibody to zolpidem and/or 4-[3-(2-N,N-dimethylamino-2-oxoethyl)-6-methylimidazo[1,2-a]pyridin-2-yl]benzoic acid and deducing the presence of or amount of zolpidem and/or 4-[3-(2-N,N-dimethylamino-2-oxoethyl)-6-methylimidazo[1,2-a]pyridin-2-yl]benzoic acid in the sample.

According to a fourth aspect of the disclosure there is a kit for detecting or determining zolpidem in a solution or an in vitro sample taken from a patient and/or 4-[3-(2-N,N-dimethylamino-2-oxoethyl)-6-methylimidazo[1,2-a]pyridin-2-yl]benzoic acid comprising an antibody of the present disclosure.

DETAILED DESCRIPTION

A first aspect of the disclosure is an immunogen of the structure

Structure I

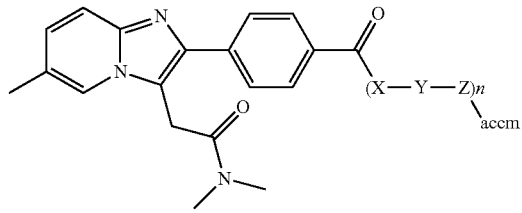

wherein —X—Y—Z— is a crosslinker and, if present, joins the carbonyl group of the phenyl ring to the accm; n=0 or 1;

accm is an antigenicity-conferring carrier material; X is a heteroatom, such as nitrogen, oxygen or sulphur; Y is a $C_1$-$C_{10}$, which in some embodiments is a $C_2$-$C_6$, substituted or unsubstituted straight-chain alkylene moiety, or arylene moiety; Z (before conjugation with the accm) is selected from a carboxy, a dithiopyridyl, a maleimide, an amino, a hydroxyl, a thiol, a thioester or an aldehyde moiety such as a carboxy moiety. In one embodiment, the immunogen is when n=0. The accm can be any material that makes the hapten-accm molecule immunogenic. The accm can be any material that makes all or part of the hapten susceptible to antibody recognition and binding. For example the accm can be a protein, a protein fragment, a synthetic polypeptide or a semi-synthetic polypeptide. In one embodiment, In one embodiment, an accm is bovine thyroid globulin (BTG). In one embodiment, the antibody is a monoclonal antibody. In another embodiment, the antibody is a polyclonal antibody.

In one embodiment of the disclosure there is an antibody raised against an immunogen of structure I, which is able to bind to an epitope of zolpidem and to an epitope of 4-[3-(2-N,N-dimethylamino-2-oxoethyl)-6-methylimidazo[1,2-a]pyridin-2-yl]benzoic acid. In one embodiment, the antibody is specific to zolpidem and possesses cross-reactivity for 4-[3-(2-N,N-dimethylamino-2-oxoethyl)-6-methylimidazo[1,2-a]pyridin-2-yl]benzoic acid. When used with reference to an antibody, the word "specific" in the context of the present disclosure refers to the analyte that is preferably bound by the antibody, as gauged by a suitable metric such as the cross-reactivity i.e. the analyte with the greatest cross-reactivity is the antibody-specific analyte and is generally given a value of 100%, with all other analytes accorded a value relative to this; in addition, as is known by one skilled in the art, for cross-reactivity to be of practical use the analyte-specific antibody must display a high sensitivity as measured by a suitable metric such as the $IC_{50}$. In one embodiment, a high sensitivity is an $IC_{50}$ of less than 50 ng/ml, in another embodiment less than 10 ng/ml, and in another embodiment less than 1 ng/ml.

In a further embodiment of the disclosure there is an antibody specific to zolpidem with a cross-reactivity for 4-[3-(2-N,N-dimethylamino-2-oxoethyl)-6-methylimidazo[1,2-a]pyridin-2-yl]benzoic acid. The cross-reactivity is greater than 5% in one embodiment, greater than 10% in another embodiment, and greater than 15% in yet another embodiment, relative to the binding of the zolpidem analyte, on the basis that the antibody has 100% specificity to zolpidem. In a further aspect, the cross-reactivity of the antibody is from 10 to 20%. The antibody can either be a polyclonal or monoclonal antibody, the monoclonal antibody being derived from the polyclonal antibody using well-known methods. If the polyclonal antibody possesses the required specificity and sensitivity and is produced in adequate quantities, development of a monoclonal antibody is unnecessary.

In a further embodiment of the disclosure there is a method of detecting or determining zolpidem and/or 4-[3-(2-N,N-dimethylamino-2-oxoethyl)-6-methylimidazo[1,2-a]pyridin-2-yl]benzoic acid in a solution or an in vitro sample taken from an individual, the method comprising detecting or determining zolpidem and/or 4-[3-(2-N,N-dimethylamino-2-oxoethyl)-6-methylimidazo[1,2-a]pyridin-2-yl]benzoic acid in a solution or an in vitro sample taken from a patient, comprising contacting the solution or sample with an antibody of any of claims 2 to 6 and a conjugate, measuring a detectable signal generated form the conjugate upon binding of the antibody to zolpidem and/or 4-[3-(2-N,N-dimethylamino-2-oxoethyl)-6-methylimidazo[1,2-a]pyridin-2-yl]benzoic acid and deducing the presence of or amount of zolpidem and/or 4-[3-(2-N,N-dimethylamino-2-oxoethyl)-6-methylimidazo[1,2-a]

pyridin-2-yl]benzoic acid in the sample. In one embodiment, the antibody is specific to zolpidem and cross-reacts with 4-[3-(2-N,N-dimethylamino-2-oxoethyl)-6-methylimidazo [1,2-a]pyridin-2-yl]benzoic acid. The cross-reactivity of the antibody to 4-[3-(2-N,N-dimethylamino-2-oxoethyl)-6-methylimidazo[1,2-a]pyridin-2-yl]benzoic acid is greater than 5% in one embodiment, greater than 10% in another embodiment, greater than 15% in yet another embodiment relative to the binding of the zolpidem analyte, on the basis that the antibody has 100% specificity to zolpidem. In a further aspect, the cross-reactivity of the antibody is from 10 to 20%. By "detecting" is meant qualitatively analyzing for the presence or absence of a substance. By "determining" is meant quantitatively analyzing for the amount of a substance.

In a further embodiment of the disclosure there is a kit for detecting or determining zolpidem and/or 4-[3-(2-N,N-dimethylamino-2-oxoethyl)-6-methylimidazo[1,2-a]pyridin-2-yl]benzoic acid. The kit comprises an antibody raised against an immunogen of structure I which binds to an epitope of zolpidem and an epitope of 4-[3-(2-N,N-dimethylamino-2-oxoethyl)-6-methylimidazo[1,2-a]pyridin-2-yl]benzoic acid. In one embodiment, the antibody is specific to zolpidem and cross-reacts with 4-[3-(2-N,N-dimethylamino-2-oxoethyl)-6-methylimidazo[1,2-a]pyridin-2-yl]benzoic acid. The cross-reactivity of the antibody to 4-[3-(2-N,N-dimethylamino-2-oxoethyl)-6-methylimidazo[1,2-a]pyridin-2-yl] benzoic acid is greater than 5% in one embodiment, greater than 10% in another embodiment, greater than 15% in yet another embodiment relative to the binding of the zolpidem analyte, on the basis that the antibody has 100% specificity to zolpidem. In a further aspect, the cross-reactivity of the antibody is from 10 to 20%. The kit may optionally include a conjugate and/or calibrator(s) and instructions for use of the kit components for detecting or determining zolpidem and/or 4-[3-(2-N,N-dimethylamino-2-oxoethyl)-6-methylimidazo [1,2-a]pyridin-2-yl]benzoic acid.

A calibrator is a molecule, usually possessing the same structure or similar structure to a target analyte and which binds to the target analyte antibody, that enables the determination of either an absolute amount of the target analyte in a sample, or a cut-off value (minimum value) of the target analyte. A minimum of two known concentrations of the calibrator may be measured. In the case of absolute quantification, a calibration or standard curve may be constructed which is made of up of several known concentrations of the calibrator, usually spanning the projected concentration range of the target analyte in the test sample.

As zolpidem is rapidly metabolised, it is possible that analysis of a sample taken from a patient, for example, 48 hours after ingestion of a standard dose of zolpidem (10 mg), will contain little or no zolpidem and it will be 4-[3-(2-N,N-dimethylamino-2-oxoethyl)-6-methylimidazo[1,2-a]pyridin-2-yl]benzoic acid that is predominantly or singly detected or measured by the method and kit as disclosed herein. Alternatively, analysis of a patient sample with the method and kits of the present disclosure within 24 hours of a standard dose of zolpidem ingestion is likely to detect and determine both zolpidem and 4-[3-(2-N,N-dimethylamino-2-oxoethyl)-6-methylimidazo[1,2-a]pyridin-2-yl]benzoic acid.

For the purposes of the disclosure, the patient sample which may be used for in vitro analysis can be hair or a peripheral biological fluid, such as serum, plasma, or urine; the solution may be, for example, a solution of cultured cells. A solution of the appropriate cultured cells would enable an in vitro assay to test for, for example, drug activity.

A hapten is a molecule that elicits an immune response only when it is conjugated to a large carrier molecule. Haptens provide defined structural epitopes and therefore are useful in raising antibodies with varying degrees of specificity to the epitopes. Once the body has generated antibodies to a hapten-carrier conjugate the hapten itself without the carrier may also be able to bind to the antibody, but it will usually not initiate an immune response. Haptens may be used in the synthesis of immunogens. Immunogen formation can proceed by various synthetic routes. Immunogen formation for the disclosure described herein involves conventional conjugation chemistry. For the purposes of the disclosure, haptens useful in preparing the immunogens of the disclosure may be synthesised in the reaction scheme shown in FIGS. 1 and 2.

To increase their immunogenicity, haptens are usually bound to carrier materials (abbreviated herein as "accm"). The hapten-carrier material will elicit an immunogenic response when administered to a host animal. Haptens may be bound to appropriate carrier materials which commonly contain poly(amino acid) segments and include polypeptides, proteins and protein fragments. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen.

The haptens used in the present disclosure can also be coupled to labelling agents to form detectable conjugates (or detection reagents). The labelling agents may be an enzyme (for example, horseradish peroxidase), a substance having fluorescent or luminescent properties or a radioactive label or a mixture thereof. Alternatively, or additionally, the luminescent substance may be a bioluminescent or chemiluminescent material. The fluorescent substance may be, for example, a monovalent residue of fluorescein or a derivative thereof.

EXAMPLES

The following examples are primarily for illustration and thus are not intended to limit the scope of protection, although the examples may include patentable features.

Preparation of Haptens, Immunogens and Conjugates

Figure 2:
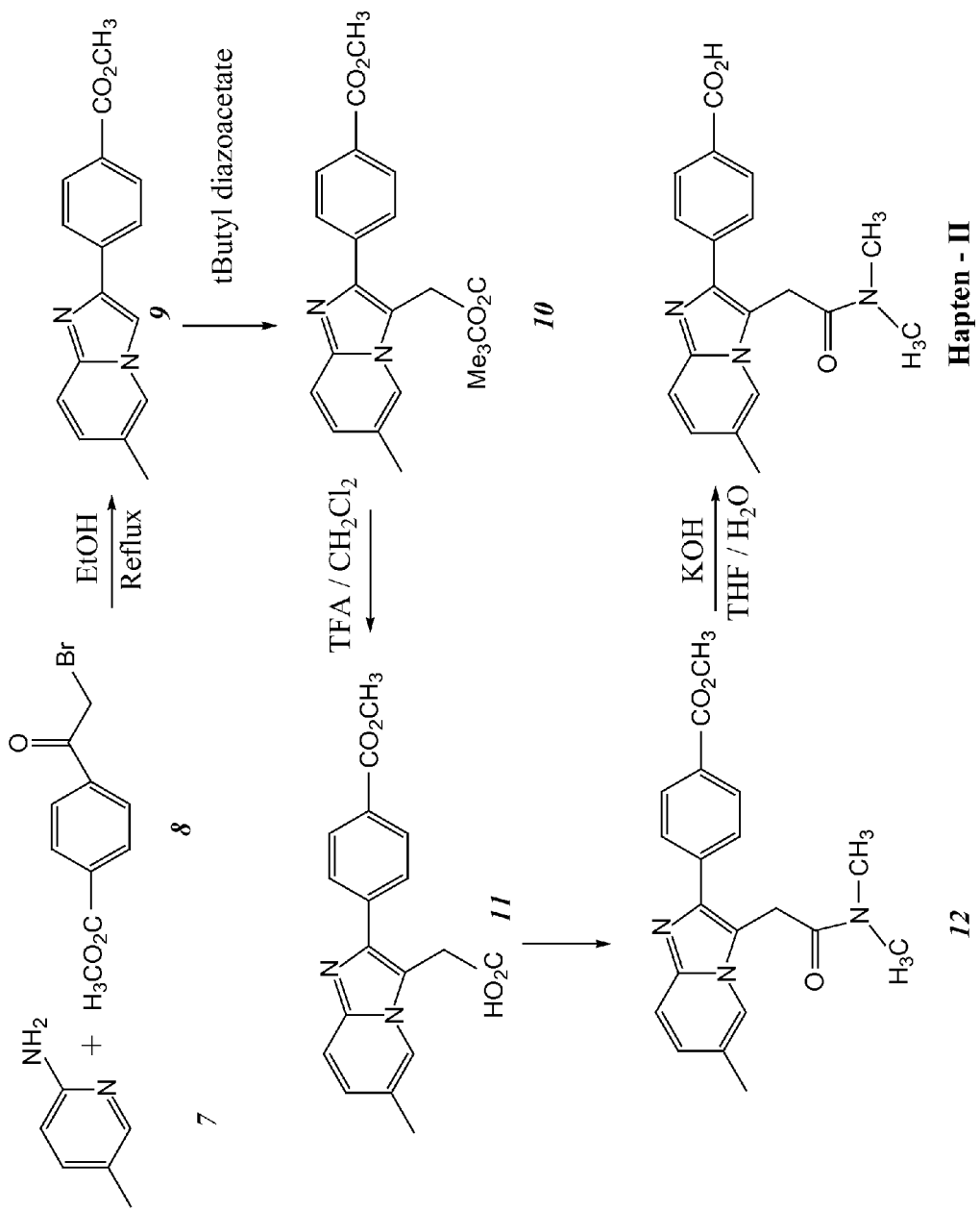
FIG. 2 shows the synthesis of hapten II.

Haptens I and II were synthesised using the reaction scheme shown in FIGS. 1 and 2 and discussed further in Examples 1-5 (for Hapten I) and Examples 9 to 14 (for Hapten II).

An immunogen of the disclosure may be made by reacting hapten I shown in FIG. 1 with N,N-dicyclohexylcarbodiimide (DCC) and then N-hydroxysuccinimide (NHS) to form an ester with a powerful leaving group. Nucleophilic attack on the carbonyl of the ester functionality by an amine group on the protein (BSA, BTG or HRP), results in conjugation via an amide bond and formation of the target immunogen. The formation of an immunogen from hapten I is discussed further in Examples 6 to 8.

Alternatively, an immunogen of the disclosure may be made by reacting hapten II shown in FIG. 2 with tri-n-butylamine and isobutyl chloroformate (IBCF) followed by the conjugation with (BSA, BTG or HRP). The formation of an immunogen from hapten II is discussed further in Examples 15 to 17.

Example 1

Preparation of methyl 2-(4-tolyl)imidazo[1,2-a]pyridine-6-carboxylate

2-Bromo-4'-methylacetophenone 2 (14.5 g, 65.1 mmol) was added to a hot solution of methyl 2-aminopyridine-5- carboxylate 1 (9.0 g, 61.1 mmol) in ethanol (280 ml). The solution was then heated at reflux for 6 h, cooled to room temperature and the white solid filtered and washed with ethanol to give methyl 2-(4-tolyl)-imidazo[1,2-a]pyridine-6-carboxylate 3 (13.9 g, 80%).

Example 2

Preparation of 2-hydroxy-2-[6-methoxycarbonyl-3-(4-tolyl)imidazo[1,2-a]pyridine-3-yl]acetic acid To a suspension of methyl 2-(4-tolyl)imidazo[1,2-a]pyridine-6-carboxylate 3 (13.31 g, 50 mmol) in dichloromethane (100 ml) was added solid glyoxylic acid monohydrate (6 g) and the mixture was heated at reflux for 4 h. The mixture was then cooled to room temperature and the white solid filtered, washed by dichloromethane, and dried under vacuum to give (14.9 g, 87%) of 2-hydroxy-2-[6-methoxycarbonyl-3-(4-tolyl)imidazo[1,2-a]pyridine-3-yl]acetic acid 4 as a white solid.

Example 3

Preparation of 2-[6-methoxycarbonyl-3-(4-tolyl)imidazo[1,2-a]pyridine-3-yl]acetic acid To a solution of 4 (8.5 g, 25 mmol) in formic acid (100 ml) under nitrogen was added 10% palladium/carbon catalyst (600 mg) and the mixture heated at reflux overnight. The mixture was cooled to room temperature, filtered and evaporated to dryness. Water (100 ml) was added and the mixture stirred for 2 h. The white precipitate was filtered, washed with water (2×50 ml) and dried to give the light brown/yellow solid 2-[6-methoxycarbonyl-3-(4-tolyl)imidazo[1,2-a]pyridine-3-yl]acetic acid 5 (7.9 g, 97%).

Example 4

Preparation of 3-Dimethylcarbamoylmethyl-2-(p-tolyl)imidazo[1,2-a]pyridine-6-carboxylate O-(1H-Benzotriazol-1-yl)-N,N,N',N'-tetramethyluronium hexafluorophosphate (7.752 g, 20.48 mmol), 1-hydroxybenzotriazole (0.92 g, 6.8 mmol) and n,n-ethyldiisopropylamine (4.8 ml, 27.76 mmol) were added to a suspension of 5 (4.4 g, 13.6 mmol) in dichloromethane (200 ml). The solution was stirred for 30 min under nitrogen, dimethylamine (2M in THF, 9.33 ml, 28.0 mmol) added and the mixture stirred at room temperature for 3 hr. Dichloromethane (200 ml) was added, and the solution washed with HCl (0.5M), saturated NaCl solution, and 10% NaHCO$_3$ solution. The organic phase was dried over MgSO$_4$ and solvent evaporated to give a light cream solid methyl 3-dimethylcarbamoylmethyl-2-(4-tolyl)imidazo[1,2-a]pyridine-6-carboxylate 6 (3.2 g, 67%).

Example 5

Preparation of 3-dimethylcarbamoylmethyl-2-(4-tolyl)imidazo[1,2-a]pyridine-6-carboxylic acid (hapten-I)

1M lithium hydroxide (84 ml, 15.4 mmol) was added dropwise to a solution of 6 (3.0 g, 8.53 mmol) in tetrahydrofuran (THF) (100 ml) and the solution stirred at room temperature overnight. Solvent was removed and the aqueous phase washed with chloroform, neutralized to pH 7 with 1M HCl and evaporated to dryness. The solid obtained was suspended in chloroform:methanol (9:1) (100 ml) and stirred for 1 h. The solid was removed by filtration, dried and purified by chromatography (chloroform:methanol, 9:1) to give hapten-I (1.67 g, 58%). NMR $^{13}$C(CD$_3$OD) (d, ppm): 172.48, 171.05, 146.92, 146.09, 139.64, 132.69, 130.77, 130.01, 128.91, 127.9, 125.43, 117.55, 115.7, 38.27, 36.64, 30.53 and 21.71. MS: Mass formula (338.1503); Calc. Mass (338.1505).

Example 6

Conjugation of Hapten-I to BSA (Immunogen-I)

To a solution of hapten-I (25.36 mg, 0.076 mmol) in DMF (1.0 ml) was added N,N-dicyclohexylcarbodiimide (DCC) (17.06 mg, 0.082 mmol) and N-hydroxysuccinimide (9.52 mg, 0.082 mmol) and the mixture stirred at room temperature overnight. The dicyclohexylurea formed was removed by filtration and the solution added dropwise to a solution of BSA (100 mg, 1.5 µmol) in 50 mM sodium bicarbonate solution (pH 8.5) (5 ml). The mixture was then stirred overnight at 4° C. The solution was then dialysed against 50 mM phosphate buffer pH 7.2 (3 changes) for 24 h at 4° C. and freeze-dried. MALDI results showed 23.66 molecule of hapten-I had been conjugated to one molecule of BSA.

Example 7

Conjugation of Hapten-I to BTG (Immunogen-II)

To a solution of hapten-I (45.7 mg, 0.135 mmol) in DMF (1.0 ml) was added N,N-dicyclohexylcarbodiimide (DCC) (30.7 mg, 0.149 mmol) and N-hydroxysuccinimide (17.13 mg, 0.149 mmol) and the mixture was stirred at room temperature overnight. The dicyclohexylurea formed was removed by filtration and the solution was added dropwise to a solution of BTG (150 mg, 2.25 µmol) in 50 mM sodium bicarbonate solution (pH 8.5) (10 ml). The mixture was then stirred overnight at 4° C. The solution was then dialysed against 50 mM phosphate buffer pH 7.2 (3 changes) for 24 h at 4° C., and freeze-dried.

Example 8

Conjugation of Hapten-I to HRP

EDC hydrochloride (10 mg) was dissolved in water (0.5 ml) and added to a solution of hapten-I (2 mg) in DMF (0.2 ml). The resulting solution was added dropwise to a solution of HRP (20 mg) in water (1 ml). Sulfo-NHS (5 mg) was added and the mixture incubated in the dark at room temperature overnight. Excess hapten was removed with double PD-10 columns (Pharmacia) in series, pre-equilibrated with PBS (pH 7.2) and the hapten-HRP conjugate dialysed overnight against 10 L of PBS (pH 7.2) at 4° C.

Example 9

Preparation of a-bromo-4-(methoxycarbonyl)acetophenone

Bromine (7.2 ml, 0.14 mol) was added dropwise to a stirred solution of methyl 4-acetylbenzoate (25.0 g, 0.14 mol) in acetic acid (300 ml). The solution was stirred at room temperature for 4 h, then poured in water (1.5 L) and stirred for 1 h. The white solid formed was filtered and washed successively with water and hexane then dried under vacuum overnight to give a-bromo-4-(methoxycarbonyl)acetophenone 8 (32 g, 89%).

Example 10

Preparation of methyl 4-(6-methylimidazo[1,2-a]pyridin-2-yl)benzoate

To a hot solution of 2-amino-5-methylpyridine 7 (8.42 g, 77.8 mmol) in ethanol (500 ml) was added 8 (20.0 g, 77.8 mmol). The solution was heated at reflux for 18 h, cooled to room temperature and the white solid filtered and washed with ethanol to give methyl 4-(6-methylimidazo[1,2-a]pyridin-2-yl)benzoate 9 (15.9 g, 76.7%).

Example 11

Preparation of methyl 4-(3-tert-butoxycarbonylmethyl-6-methyl)imidazo[1,2-a]pyridin-2-ylbenzoate Tert-butyl diazoacetate (5 ml, 35.15 mmol) then copper powder (2.5 g) were gradually added to a refluxing solution of 9 (5.0 g, 18.8 mmol) in anhydrous toluene (150 ml). After a further 3 h of reflux, the mixture was cooled to room temperature, the suspension filtered and dried. Purification by column chromatography on silica gel (ethyl acetate-hexane, 1:1) gave methyl 4-(3-tert-butoxycarbonylmethyl-6-methylimidazo[1,2-a]pyridin-2-yl)benzoate 10 (3.35 g, 47%).

Example 12

[2-(4-carboxymethylphenyl)-6-methylimidazo[1,2-a]pyridin-3-yl]acetic acid

A solution of 10 (3.1 g, 8.15 mmol) in dichloromethane (50 ml) was added to trifluoroacetic acid (25 ml). Following stirring at room temperature for 2 h the solution was concentrated to dryness. Potassium carbonate (10%) solution (100 ml) was added and the solution washed with diethyl ether (2×50 ml) and acidified to pH 6 with HCl (6M). The precipitate was filtered, washed with diethyl ether and recrystallized to give [2-(4-carboxymethylphenyl)-6-methylimidazo[1,2-a]pyridin-3-yl]acetic acid 11 as a white solid (1.65 g, 62%).

Example 13

Preparation of methyl 4-(3-N,N-dimethylcarbomoylmethyl-6-methyl imidazo[1,2-a]pyridin-2-yl)benzoate Methyl 4-(3-N,N-dimethylcarbamoylmethyl-6-methyl imidazo[1,2-a]pyridin-2-yl)benzoate was prepared from the carboxylic acid 11 (1.5 g, 4.6 mmol), O-(1H-benzotriazol-1-yl)-N,N,N',N'-tetramethyluronium hexafluorophosphate (2.61 g, 6.86 mmol), 1-hydroxybenzotriazole (312.0 mg, 2.26 mmol), N,N-ethyldiisopropylamine (1.2 g, 9.2 mmol) and dimethylamine (2M in THF, 1.55 ml, 4.64 mmol) in a similar manner to that described for the synthesis of 6 (Example 4). 1.33 g of methyl 4-(3-N,N-dimethylcarbamoylmethyl-6-methyl imidazo[1,2-a]pyridin-2-yl)benzoate 12 was obtained (82%).

Example 14

Preparation of 4-(3-N,N-dimethylcarbamoylmethyl-6-methylimidazo[1,2-a]pyridin-2-yl)benzoic acid (hapten-II)

1M Lithium hydroxide (33.6 ml, 6.16 mmol) was added dropwise to 12 (1.2 g, 3.41 mmol) in tetrahydrofuran (THF) (30 ml) and the solution stirred at room temperature overnight. Solvent was removed and the aqueous phase washed with chloroform, neutralized to pH 7 with 1M HCl and dried. The solid obtained was suspended in a mixture of chloroform:methanol 9:1 (100 ml) and stirred for 1 h. The solid was filtered, dried and purified by chromatography on silica gel (chloroform-methanol, 9:1) to give hapten-II (0.85 g, 74%). MS: Mass formula (338.1505); Calc. Mass (338.1523).

Example 15

Conjugation of Hapten-II to BSA (Immunogen-III)

Tri-n-butylamine (31.42 µl, 0.066 mmol) and isobutyl chloroformate (IBCF) (17.02 µl, 0.132 mmol) was added to a 0° C. solution of hapten-II (40.48 mg, 0.06 mmol) in DMF (3 ml) in under nitrogen. After 15 mins the mixture was added dropwise to a cooled solution of BSA (100 mg) in 100 mM sodium bicarbonate pH 8.5 (10 ml) and the mixture stirred at 4° C. overnight. The solution was then dialysed against 50 mM phosphate buffer pH 7.2 (3 changes) for 24 h at 4° C., and freeze-dried. MALDI results showed 29.1 molecule of hapten-II to one molecule of BSA.

Example 16

Conjugation of Hapten-II to BTG (Immunogen-IV)

Tri-n-butylamine (53.1 µl, 0.223 mmol) and isobutyl chloroformate (IBCF) (28.78 µl, 0.223 mmol) was added to a 0° C. solution of hapten-II (68.5 mg, 0.203 mmol) in DMF (3 ml) in under nitrogen. After 15 mins the mixture was added dropwise to a cooled solution of BTG (150 mg) in 100 mM sodium bicarbonate pH 8.5 (10 ml) and the mixture stirred at 4° C. overnight. The solution was then dialysed against 50 mM phosphate buffer pH 7.2 (3 changes) for 24 h at 4° C., and freeze-dried.

Example-17

Conjugation of Hapten-II to HRP

Tri-n-butylamine (38 ml) and isobutyl chloroformate (IBCF) (2 ml) was added to a 0° C. solution of hapten-II (2 mg) in DMF (200 ml) under nitrogen. The mixture was stirred for 10 mins, added dropwise to a cooled solution of HRP (200 mg) in water (800 ml) and incubated in the dark at room temperature overnight. Excess hapten was removed with double PD-10 columns (Pharmacia) in series, pre-equilibrated with PBS at pH 7.2, and the hapten-HRP conjugate dialysed overnight against 10 L of PBS at pH 7.2 at 4° C.

General Procedure for MALDI-TOF Analysis of Immunogens

In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of Sinapinic acid and bovine serum albumin (Fluka) was used as an external calibrant.

Preparation of Antisera

In order to generate polyclonal antisera, an immunogen of the present disclosure is mixed with Freund's adjuvant and the mixture is injected into a host animal, such as rabbit, sheep, mouse, guinea pig or horse. Sheep are useful as the host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunising an animal, such as a mammalian animal, by repeated administration of an immunogen. The serum from the immunised animal is collected when the antibody titre is sufficiently high. A conjugate is added to a sample containing the target analyte and the raised antibodies, and the conjugate and analyte compete for binding to the antibodies. The process may comprise fixing said serum antibodies to a backing substrate such as a polystyrene solid support or a biochip. The antibodies can be polyclonal or monoclonal, monoclonal antibodies being obtainable from polyclonal sera using standard techniques. The signal emitted in the immunoassay is proportionate to the amount of conjugate bound to the antibodies which in turn is inversely proportionate to the analyte concentration. The signal can be detected or quantified by comparison with a calibrator.

Example 18

Development of ELISAs for Zolpidem

Analogues of zolpidem derivatised at the 4'-phenyl ring were coupled by way of a crosslinker to bovine thyroglobulin (BTG). The resulting immunogens were administered separately to adult sheep on a monthly basis to provide target-specific polyclonal antisera. IgG was extracted from the antisera via caprylic acid/ammonium sulphate precipitation of immunoglobulin. Microtitre plates were coated with antibody (125 µl/well) in coating buffer (10 mM Tris pH 8.5) at 37° C. for 2 h. The plates were then washed 4 times over 10 mins with working strength TBST. 50 µl of sample/standard (zolpidem, Sequioa SRP00500z; alpidem, TRC A575560; zaleplon, Sequioa SRP00300z; zopiclone, Sequioa SRP02000z; zolpidem Carboxylic Acid, Randox LK865 and zolpidem carboxylic acid, Randox LK855) was added to the appropriate wells in triplicate, followed by 75 µl of hapten-HRP conjugate and incubated at 25° C. for 1 h. The plates were then washed and 125 µl of TMB (Randox, 4380-15) was added to each well and left at room temperature for 20 mins in the dark. The reaction was stopped using 125 µl of 0.2M sulphuric acid. The absorbances were read at 450 nm with an ELISA microplate reader (BIO-TEK Instruments, Elx800) and the means calculated. Antibody specificity and sensitivity were then determined.

Results

Figure 3:
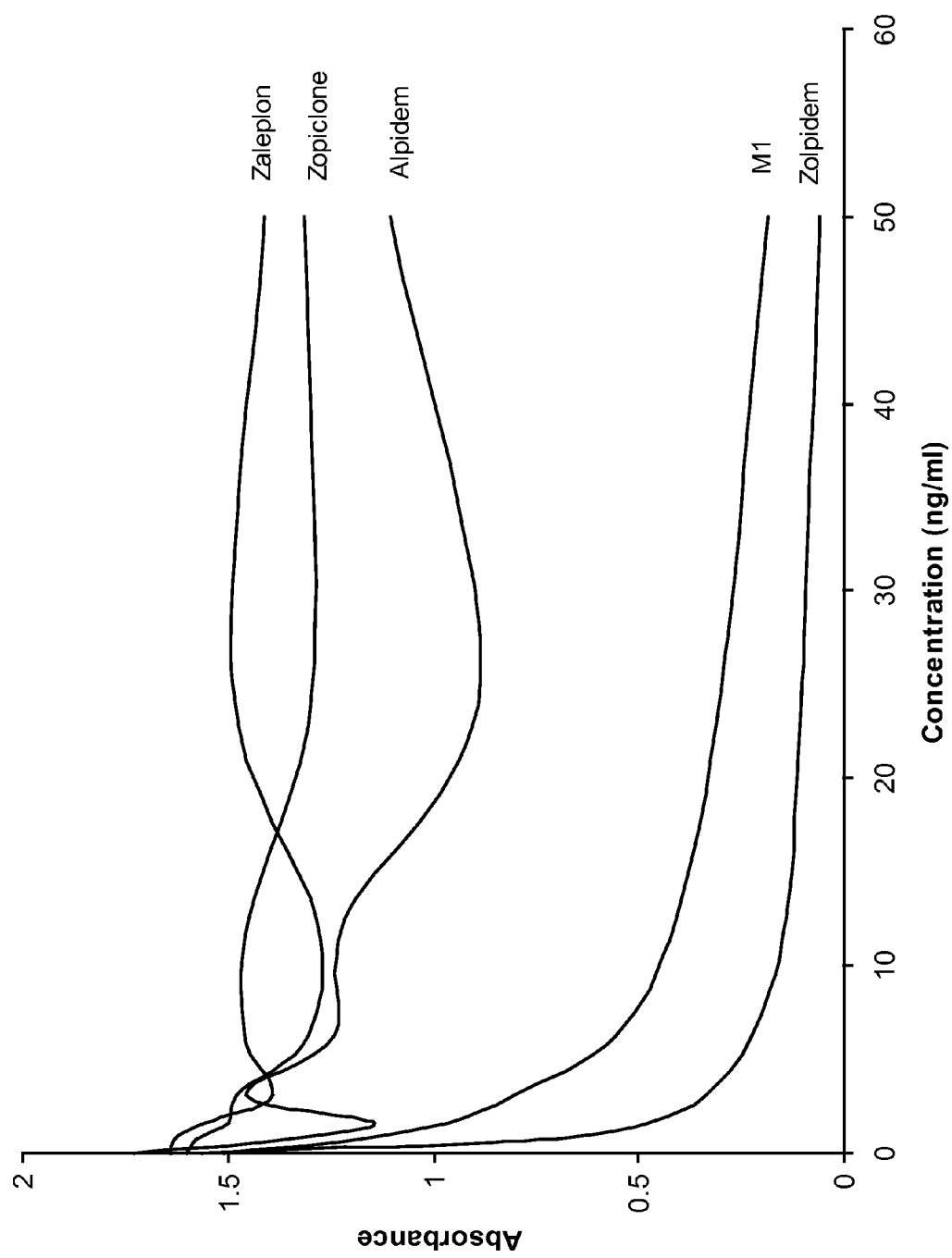
FIG. 3 shows the antibody concentration-response curves for zolpidem, its main metabolite and structurally-related analytes.

Competitive ELISA results in Table 1 and FIG. 3 highlight the specificity of the antibody of the disclosure towards zolpidem and cross-reactivity towards 4-[3-(2-N,N-dimethylamino-2-oxoethyl)-6-methylimidazo[1,2-a]pyridin-2-yl]benzoic acid. The antibody does not cross-react with several common structurally-related drugs. The disclosure, through its unique immunogens and antibodies, thus enables methods and kits able to detect and determine zolpidem and/or 4-[3-(2-N,N-dimethylamino-2-oxoethyl)-6-methylimidazo[1,2-a]pyridin-2-yl]benzoic acid with high sensitivity.

TABLE 1

| | Zolpidem | M1 | M2 | Alpidem | Zaleplon | Zopiclone |
|---|---|---|---|---|---|---|
| $IC_{50}$ (ng/ml) | 0.63 | 3.33 | >500 | >>50 | >>50 | >>50 |
| % CR | 100 | 18.6 | <0.13 | <<1.26 | <<1.26 | <<1.26 |

% CR = percentage cross-reactivity based on 100% specificity to zolpidem.

It will be understood by those having skill in the art that changes may be made to the details of the above-described embodiments without departing from the underlying principles presented herein. Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein.

Any method disclosed herein comprises one or more steps or actions for performing the described method. The method steps and/or actions may be interchanged with one another. In other words, unless a specific order of steps or actions is required for proper operation of the embodiment, the order and/or use of specific steps and/or actions may be modified.

The claims following this Detailed Description are hereby expressly incorporated into this Detailed Description, with each claim standing on its own as a separate embodiment. This disclosure includes all permutations of the independent claims with their dependent claims. Recitation in the claims of the term "first" with respect to a feature or element does not necessarily imply the existence of a second or additional such feature or element. Embodiments of the disclosure in which an exclusive property or privilege is claimed are defined as follows.

The invention claimed is:
1. A method of detecting or determining zolpidem and/or 4-[3-(2-N,N-dimethylamino-2-oxoethyl)-6-methylimidazo[1,2-a]pyridin-2-yl]benzoic acid in a solution or an in vitro sample taken from a patient, comprising:
contacting the solution or sample with an antibody raised against an immunogen of the structure I:

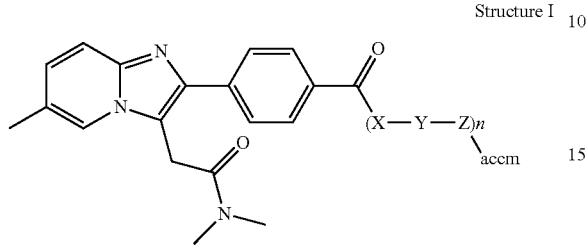

Structure I wherein,
accm is an antigenicity conferring carrier material; n=0 or 1; X is a heteroatom; Y is a $C_{1-10}$, substituted or unsubstituted straight-chain alkylene or arylene moiety; Z is, before conjugation with the accm, at least one of carboxy, a dithiopyridyl, a maleimide, an amino, a hydroxyl, a thiol, a thioester or an aldehyde moiety; and
a conjugate;
measuring a detectable signal generated from the conjugate upon binding of the antibody to zolpidem and/or 4-[3-(2-N,N-dimethylamino-2-oxoethyl)-6-methylimidazo[1,2-a]pyridin-2-yl]benzoic acid and deducing the presence of or amount of zolpidem and/or 4-[3-(2-N,N-dimethylamino-2-oxoethyl)-6-methylimidazo[1,2-a]pyridin-2-yl]benzoic acid in the sample, wherein the antibody has more than 5% cross-reactivity with 4-[3-(2-N,N-dimethylamino-2-oxoethyl)-6-methylimidazo[1,2-a]pyridin-2-yl]benzoic acid based on 100% specificity to zolpidem.

2. The method as recited in claim 1, wherein the heteroatom is one of nitrogen, oxygen or sulphur.

3. The method as recited in claim 1, wherein Y is a $C_{2-6}$.

* * * * *